United States Patent

Jentzen

[11] Patent Number: 5,913,843
[45] Date of Patent: Jun. 22, 1999

[54] DAMPENING DEVICE FOR SPRING MOVEMENT

[76] Inventor: S. William Jentzen, 3000 Artesian Dr., Cedar Creek, Tex. 78612

[21] Appl. No.: 08/980,136
[22] Filed: Nov. 26, 1997
[51] Int. Cl.⁶ .................................................. A61M 5/00
[52] U.S. Cl. .......................... 604/110; 604/198; 604/195
[58] Field of Search ................... 604/218, 110, 604/134, 181, 186, 187, 207, 226, 240, 242, 243, 246, 195, 198; 128/919

[56] References Cited

U.S. PATENT DOCUMENTS

| 5,049,133 | 9/1991 | Villen Pascual | 604/110 |
| 5,561,694 | 10/1996 | Clemens et al. | 604/110 |
| 5,613,952 | 3/1997 | Pressley, Sr. et al. | 604/110 |
| 5,792,107 | 8/1998 | Petrocelli | 604/110 |
| 5,800,395 | 9/1998 | Botich et al. | 604/110 |
| 5,880,403 | 9/1998 | Pressley, Sr. et al. | 604/195 |

*Primary Examiner*—Corrine McDermott
*Assistant Examiner*—LoAn H. Thanh
*Attorney, Agent, or Firm*—Beirne Maynard & Parsons, L.L.P.

[57] ABSTRACT

Timing of movements of a spring between a stressed and a free state is delayed by dampening the spring movement through incorporation of a component having a restricted access diameter whereby frictional contact of the spring through the component will prolong the time required to move the spring between states to enhance control of the spring actuation.

2 Claims, 4 Drawing Sheets

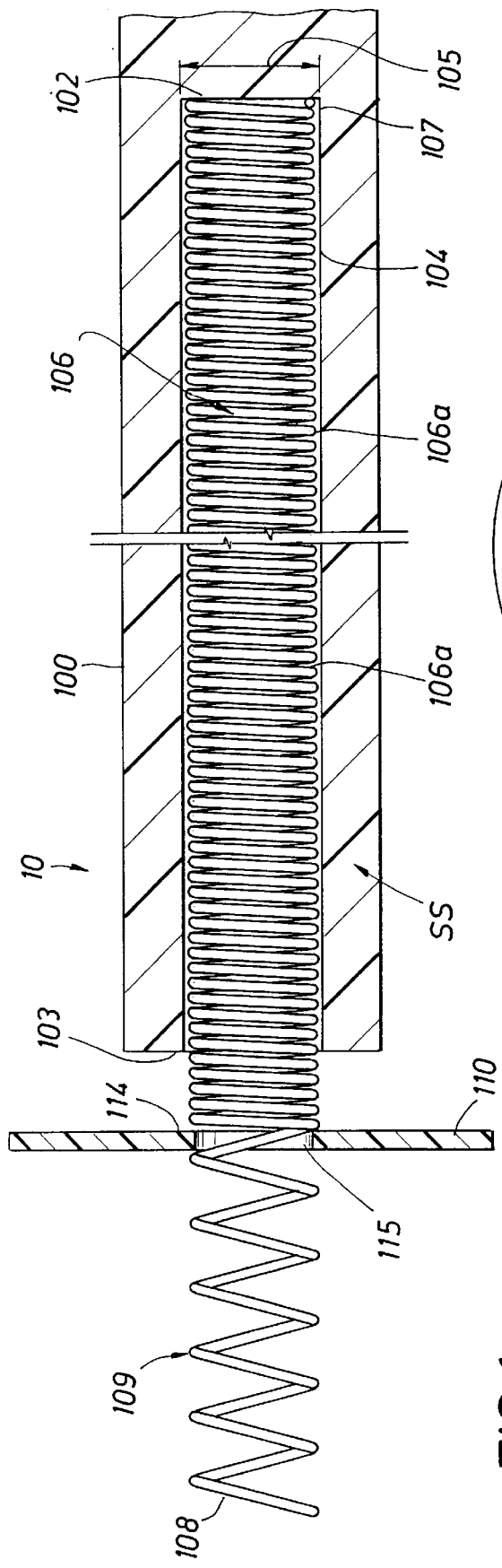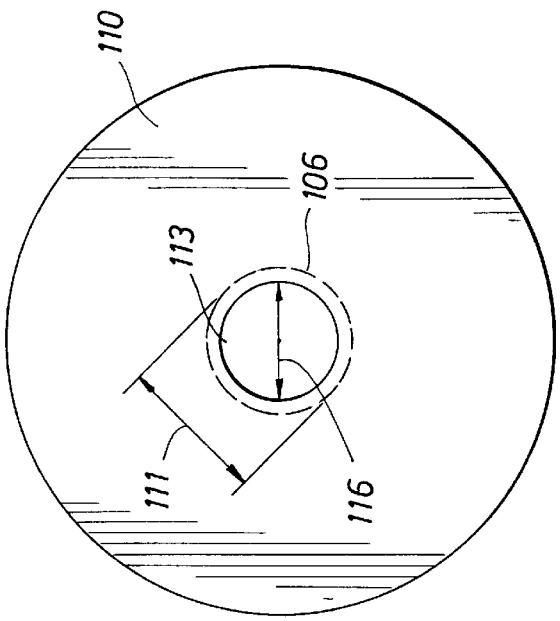

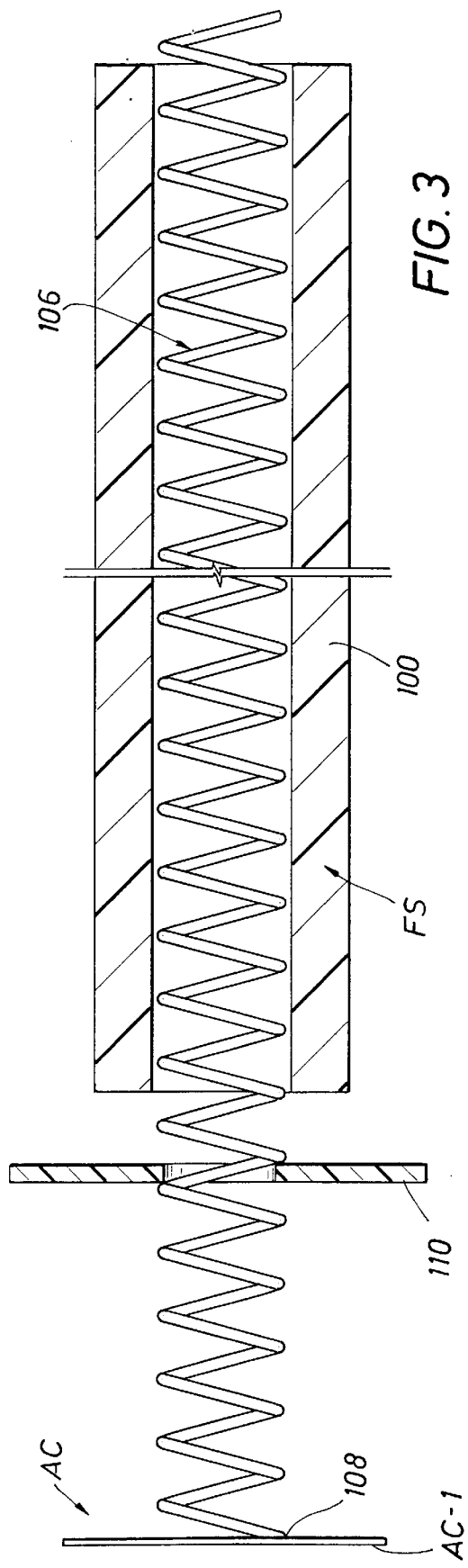

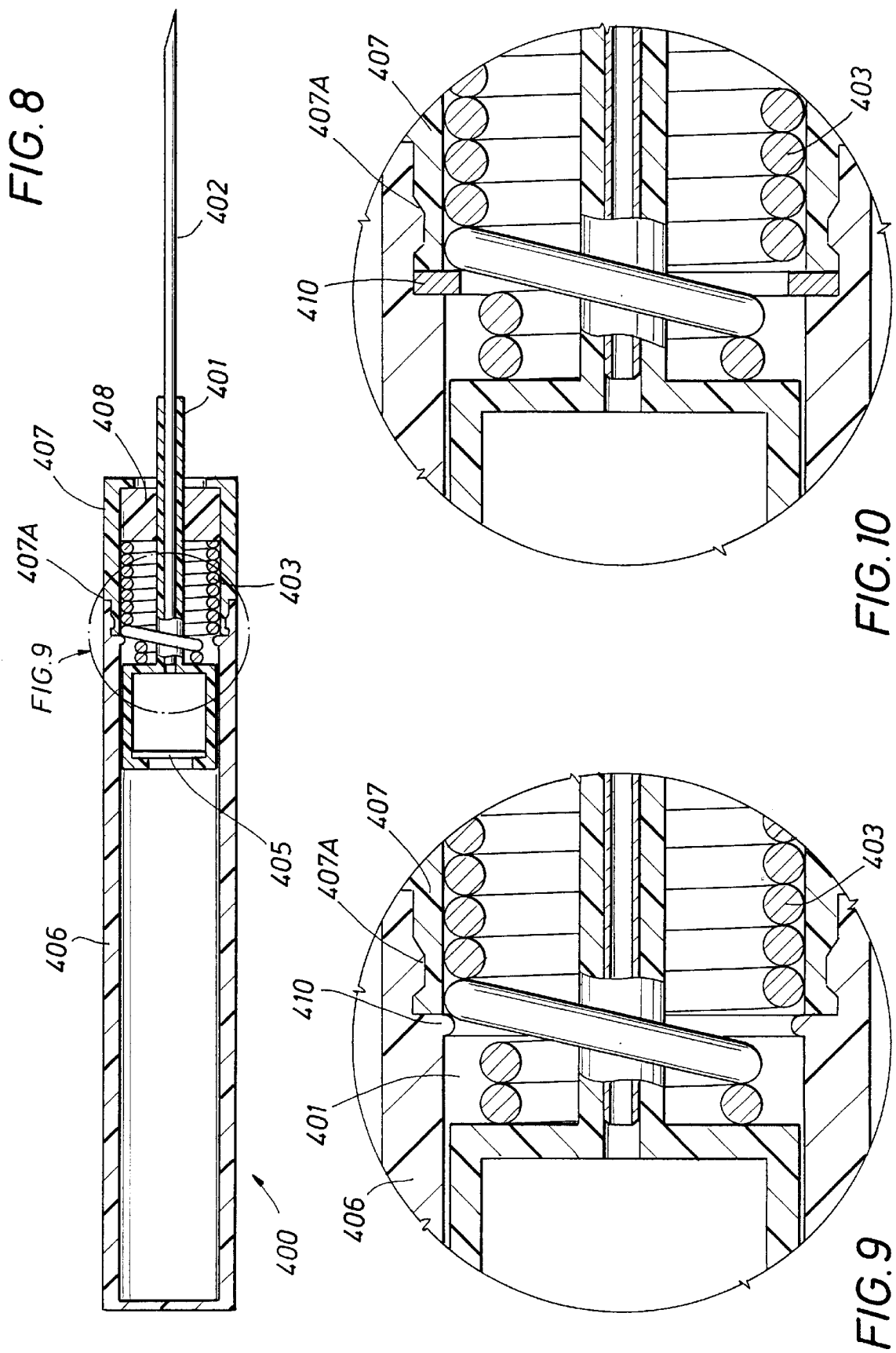

DAMPENING DEVICE FOR SPRING MOVEMENT

BACKGROUND OF THE INVENTION

1. Field of the Invention

The invention relates to a device for controlling the time of actuation of a spring which may be incorporated, for example, in a disposable safety syringe or catheter.

2. Brief Description of the Prior Art

Springs are commonly used as a power source for the actuation of an auxiliary component or device. However, springs have one characteristic which is unattractive in many applications. The amount of force which is generated by the spring when it is moved between stressed and free states is a largely linear function of the amount by which the spring has been compressed or expanded from its free state. Accordingly, when the spring is released, the spring generates its maximum amount of force at the instant of release, and the force declines linearly as the spring recovers to its free state.

In many applications, this sudden acceleration is undesirable. For example, in U.S. Pat. No. 5,053,010, entitled "Safety Syringe with Retractable Needle", issued Oct. 1, 1991, there is shown and disclosed an improved safety syringe with retractable needle which allows retraction of the needle into a hollow plunger by forward pressure on the plunger after fluid is driven from the syringe into the patient. The syringe includes a hollow plunger which is inserted into one end of a cylindrical barrel and a hollow needle attached to the other end of the barrel. Actuation of the plunger subsequent to injection of the fluid within the barrel into the patient will cause the compressive bias within a spring mechanism to be applied against a carrier for the shifting of the needle into the interior of the hollow plunger. If liquid, such as medicine, still is contained within the interior of the hollow needle during the retraction step, the sudden acceleration of the needle in a backward-like direction into the interior of the plunger may, depending upon on the amount, viscosity, temperature, pressure and other variables, cause or contribute to considerable quick ejection out of the open end of the needle of such fluid, resulting in spillage onto the patient, operator, or floor immediate the area of positioning of the syringe. A similar situation could occur when the device to be actuated by the spring biasing mechanism is provided in the form of a catheter. The present invention addresses the problems set forth above.

BRIEF DESCRIPTION OF THE DRAWINGS

FIG. 1 is a horizontal cross-sectional view of the device of the present invention, illustrating a compressed spring in its stressed state being moved through a dampening means during operation.

FIG. 2 is a cross-sectional view of the collar component of the device of FIG. 1.

FIG. 3 is a view similar to that of FIG. 1, with a spring shown in expanded state actuating against the wall of an auxiliary component, with the spring shown in its free state.

FIG. 4 is a horizontal cross-sectional view of a safety syringe incorporating the device of the present invention.

FIG. 8 is a horizontal cross-sectional view of a catheter incorporating the device of the present invention.

FIG. 9 is a horizontal sectional view, constituting an enlargement of a portion of the device shown in FIG. 8.

FIG. 10 is an alternative preferred embodiment of the design of the device of the present invention as shown in FIGS. 8 and 9.

SUMMARY OF THE INVENTION

Figure 5:
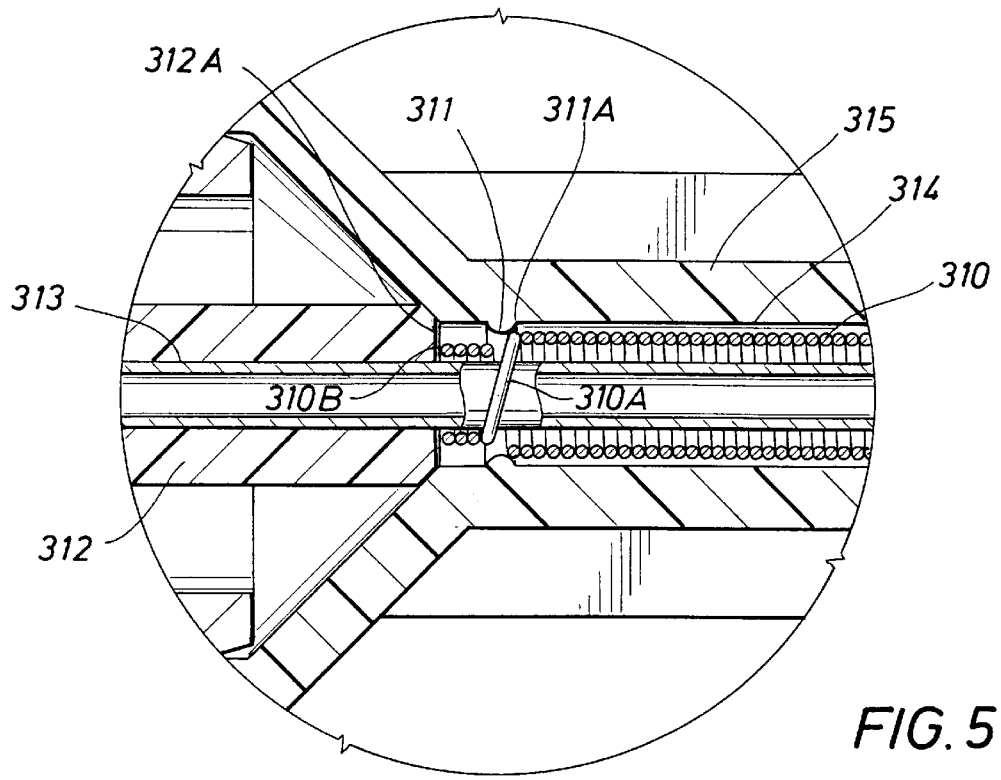
FIG. 5 is an enlarged detail view of the device of the present invention shown in the safety syringe of FIG. 4.

The present invention provides a device for delivering energy which is stored in a spring which is to be moved between stressed and free states. The "stressed" state may be either compressed or expanded position or state. "Free" state is that condition that the biasing spring is in subject to substantially complete activation and may also be compressed or expanded in that condition. Thus, the "stressed" state is that state of the biasing spring prior to actuation, while the "free" state is that condition of the biasing spring subsequent to a completion of actuation.

The device includes a housing having an inner cylindrical wall of a given diameter. A continuous length of compressible spring, preferably provided in a continuously coiled or spiraled length, is stored in the housing and is positionable therein and along at least a portion of the wall in one of the stressed and free states, with the spring having an outer surface of a given diameter which is disposed along the continuous length of the spring. Means are provided for selectively actuating movement of the spring from one of the stressed and free states to the other of the said states and within the housing. Dampening means are provided for controlling the rate of movement, or the time of the movement, of the spring between the states and the actuation of the auxiliary component.

The dampening means may preferably comprise an elongated collar which is operatively positionable relative to the housing and includes an inner wall along the entire elongate. The collar has first and second open ends through which the spring is disposed. The collar further defines a restricted diameter passageway therethrough with the diameter of the restricted passageway being less than the diameter of the outer surface of the spring, such that the outer surface of the coils of the spring frictionally engages the inner wall of the collar to delay movement of the spring therethrough.

The device of the present invention may be incorporated into a non-reusable retractable safety syringe. Such a syringe may be provided wherein a cylindrical barrel, having first and second barrel ends and an inner diameter wall, defines a chamber which further receives fluid, such as medicine. A plastic hollow plunger extends into the barrel through the first end and is moveable from an expandable position toward an expended position. A hollow needle is secured relative to the second end of the barrel and a spring component incorporating the dampening means of the present invention is initially compressed in stressed state to provide energy for moving the hollow needle interior of the barrel and within the plastic hollow plunger subsequent to the plunger being moved to the expended position.

The invention may also be utilized in a catheter in which a hollow needle may telescopically contract relative to an outer cylindrical housing subsequent to use.

DESCRIPTION OF THE PREFERRED EMBODIMENTS

Now, with first reference to FIG. 1, there is shown the device 10 in horizontal, cross-sectional view. The device 10 includes an outer elongated cylindrical housing 100 having at one end thereof a closed end surface 102 and at the opposite end an opening 103 through which may be introduced during manufacture, a length of compressible spring 106, typically made of a metallic or plastic substance sufficient to be moved from stressed to free states without breakage, and further, which is capable of storing compressive energy therethrough. The spring 106 has a terminating first end 107 which is housed within the housing 100 against the closed end 102.

As shown in FIG. 1, the spring 106 is positioned within the housing 100 in stressed state SS. The housing has a diameter indicated by line 105. In the stressed state SS and within the housing 100, the outer surface 109 of the spring 106 may, or may not, come into contact with the inner wall 104 of the housing 100, but if there is contact, it is casual and not sufficient to interfere with spring actuation, as the housing 100 only serves to contain the spring, not interfere with its operation. The spring 106 has a second end 108 which typically will abut against an auxiliary component AC (FIG. 3) having an inner wall AC-1. The spring 106 may thus cause movement of the auxiliary component AC, or the housing 100, depending upon component organization and a particular operation at hand.

A collar 110 is provided which, as shown, may be of circular or similar shape, the particular shape of the collar 110 not being particularly critical to the present invention. The collar 110 has an opening 115 therethrough through which the spring 106 may pass. The collar 110 has first and second open ends 114, 115 through which the coils or loops 106A of the spring may pass during actuation.

Now with reference to FIG. 2, the spring 106 has an outside diameter 111 and the collar 110 has a restricted passageway 116 therethrough such that the diameter of the restricted passageway 116 is somewhat smaller than the spring outside diameter 111 and, preferably, the housing diameter 105 (assuming that the collar 110 and the housing 100 are in lateral alignment, as shown in FIG. 1). As the spring moves from the position shown in FIG. 1 to the position 20 shown in FIG. 3, it will now be appreciated that the coils 106A of the spring 106 must pass through the opening, or restricted passageway 116 and the collar 110. The friction resulting between the contact of the coils 106A and the inner wall 113 of the collar 110 will "meter" or dampen movement of the spring 106 therethrough, causing a time delay of the actuating force in the spring 106. The difference in the diameter of the spring 106 and that afforded through the restricted passageway 116 and defined by the inner wall 113 thereof controls a rate of recovery of the spring 106 by requiring the coils or loops 106A of the spring 106 to wind its way through the orifice, metering means, or collar 110.

It has been experimentally determined that, for instance, a compression spring with an outside diameter of 0.285 inches will recover almost instantaneously through a spring controlled orifice with a diameter equal to or larger than 0.285 inches. As the spring control orifice is reduced in relative diameter, the spring recovery rate declines and the recovery period increases. With an orifice diameter of 0.266 inches (a 7% occlusion) the recovery period of the spring increases to about ½ second. With an orifice diameter of 0.242 inches (a 15% occlusion), the recovery period of the spring increases to almost 2 seconds. Thus, by controlling the orifice, the time required for the winding of the spring from stressed to free state may be dramatically extended, while not adversely affecting the compressive biased energy stored or to be stored in the spring.

Now with reference to FIG. 4, there is shown a non-reusable retractable safety syringe 300 incorporating the device 10 of the present invention. A cylindrical barrel 301 is provided which receives at a first open barrel end 303 a hollow plunger 307. The cylindrical barrel 301 also has a second barrel open end 302 through which is projected a retractable hollow needle 309 which is biased towards telescopically contracted state relative to the barrel 301 and plunger 307 by means of a compressed spring 310. The syringe 300 includes a chamber 305 therein for receipt of fluid which is ejected out of the open end 309A of the needle 309 during operation. An elastomeric seal 306 is disposed on one end of the hollow plunger 307 for movements against a smooth inside diameter wall 304 of the cylindrical barrel 301 to eject liquid completely out of the syringe 300.

Now with reference to FIG. 5, the dampening means is shown as provided by means of a collar or doughnut 311 which is geometrically provided in the form of a half-circle having a first inner surface 311A for contacting engagement of a first coil surface 310A of a spring 310, with one end 310B of the spring 310 shouldered against a surface 312A of a needle carrier 312 disposed around one end of a hollow needle 313. The first surface 311A of the collar 311 extends inwardly of the inner wall 314 of a companion housing member 315 to resist movements of the spring coils 310A there across.

Figure 6:
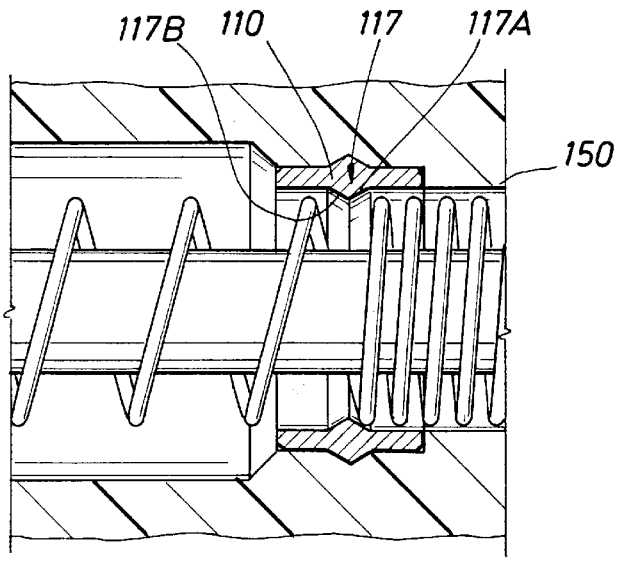
FIG. 6 is a horizontal sectional view of an alternative preferred embodiment of the device shown in FIG. 5.

A similar design for a metering means is shown in FIG. 6 in which the collar 110 is provided with a "V"-shaped orifice 117 having angled surfaces 117A and 117B disposed approximately 45° offset from a center line 150 of a housing component (not shown).

Figure 7:
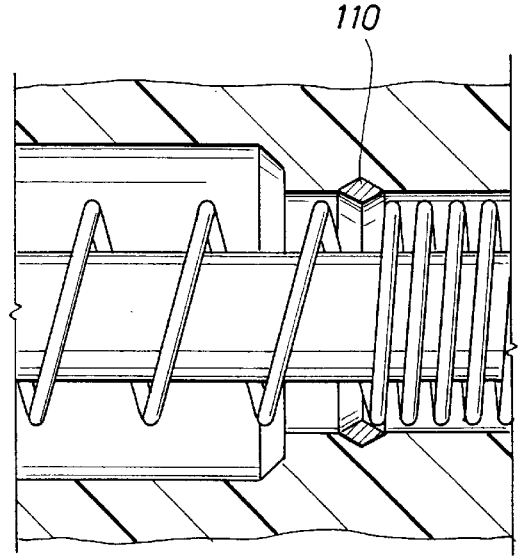
FIG. 7 is a view similar to that of FIG. 6, showing yet another alternative preferred embodiment of the present invention.

Likewise, as shown in FIG. 7, the collar 110 may actually be angled or bevelled surfaces inwardly disposed on the housing for the spring element.

Now referring to FIGS. 8, 9, and 10, there is shown the incorporation of the present invention into a catheter 400. The catheter 400 is typical of such devices, and it comprises a hollow cylindrical body 406 and a catheter body top 407 which may be secured to the body 406 by threads 407A, or by other convenient means. A spring 403 is provided therein having one end resting against a needle carrier 401 with a collar 410 of the design shown in FIG. 5 being disposed on the body 406. A clamp 408 is disposed interiorly of the housing member 407, and when the clamp is released, the needle assembly may retract into the catheter body as a result of the biased compressive stress forces contained within the spring being metered through the metering means 410 to shift the housing 401 for the needle 402 inwardly of the cylindrical body 406. A semi-permeable membrane 405, of known construction, is provided. The clamping device 408 may be one of any number of known devices, such as that shown in U.S. Pat. No. 5,501,675 to Erskine.

Although the invention has been described in terms of specified embodiments which are set forth in detail, it should be understood that this is by illustration only and that the invention is not necessarily limited thereto, since other alternative embodiments and operating techniques will become apparent to those skilled in the art in view of the disclosure. Accordingly, modifications are contemplated which can be made without departing from the spirit of the described invention.

What is claimed and desired to be secured by Letters Patent is:

1. A non-reusable safety syringe comprising:
   (a) a cylindrical barrel having first and second barrel ends and an inside diameter wall there between;

(b) a chamber for receipt of fluid within said barrel and between said first and second barrel ends;

(c) a plastic hollow plunger extendable into said barrel through the first end of said barrel, and selectively moveable from an expanded position toward an expended position immediate the second barrel end;

(d) a hollow needle in secured relationship relative to the second end of the barrel; and movable into the plunger;

(e) spring biasing means, in initially secured relationship relative to the second end of the barrel for biasing the needle towards the hollow plunger; and (f) dampening means for controlling the time of effective movement of said spring biasing means as the hollow needle is moved into the plunger, whereby upon movement of said plunger to the expended position, fluid is discharged and the hollow needle is thereafter moved into the plunger.

2. The safety syringe of claim 1 wherein the dampening means comprises an elongated collar operatively positionable relative to said barrel and including an inner wall defining a restricted diameter passageway therethrough, the diameter of said restricted passageway being less than the diameter of the outer surface of said spring biasing means, whereby the outer surface of said spring biasing means frictionally engages an inner wall of said collar to delay movement of said spring biasing means therethrough during activation of movement of said hollow needle toward said hollow plunger.

* * * * *